United States Patent [19]

Hudrlik

[11] Patent Number: 5,156,149

[45] Date of Patent: Oct. 20, 1992

[54] SENSOR FOR DETECTING CARDIAC DEPOLARIZATIONS PARTICULARLY ADAPTED FOR USE IN A CARDIAC PACEMAKER

[75] Inventor: Terrence R. Hudrlik, Fridley, Minn.

[73] Assignee: Medtronic, Inc., Minneapolis, Minn.

[21] Appl. No.: 827,858

[22] Filed: Jan. 30, 1992

Related U.S. Application Data

[63] Continuation of Ser. No. 566,636, Aug. 10, 1990, abandoned.

[51] Int. Cl.$^5$ .............................................. A61N 1/37
[52] U.S. Cl. .................................................. 128/419 PG
[58] Field of Search .................... 128/419 PG, 419 PT

[56] References Cited

U.S. PATENT DOCUMENTS

| | | | |
|---|---|---|---|
| 3,835,865 | 9/1974 | Bowens | 128/419 PG |
| 3,877,438 | 4/1975 | Cannon | 128/419 PG |
| 3,999,556 | 12/1976 | Alferness | 128/419 PG |
| 4,055,189 | 10/1977 | Auerbach et al. | 128/419 PG |
| 4,114,627 | 9/1978 | Lewyn et al. | 128/419 PT |
| 4,170,999 | 10/1979 | Allen et al. | 128/419 PG |
| 4,337,779 | 7/1982 | Spevak et al. | 128/691 |
| 4,357,943 | 11/1982 | Thompson et al. | 128/419 PG |
| 4,365,639 | 12/1982 | Goldreyer | 128/419 PG |
| 4,373,531 | 2/1983 | Wittkampf et al. | 128/419 PG |
| 4,532,931 | 8/1983 | Mills | 128/419 PG |
| 4,537,201 | 8/1983 | Lewe-Vedove et al. | 128/419 PG |
| 4,543,956 | 10/1985 | Herscovici | 128/419 PG |
| 4,664,116 | 5/1987 | Shaya et al. | 128/419 PT |
| 4,759,367 | 7/1988 | Callaghan | 128/419 PG |
| 4,768,511 | 9/1988 | DeCote, Jr. | 128/419 PG |
| 4,827,934 | 5/1989 | Ekwall | 128/419 PG |

OTHER PUBLICATIONS

Biology of the Uterus, edited by Ralph M. Wynn pp. 466–481, publication date unknown.
"Voltage-Clamp Studies on Uterine Smooth Muscle" by Nels G. Anderson, Jr. published in the Journal of General Physiology, vol. 54, No. 2, Aug., 1969 pp. 145–165.
"The Action Potential in the Smooth Muscle of the Guinea Pig Teania Coli and Ureter Studied by the Dougle Sucrose-Gap Method" by H. Kuriyama et al., published in The Journal of General Physiology, vol. 55, No. 2, Feb. 1970.
"Amplifiers and Signal Processing", Medical Instrumentation-Application and Design by Webster et al., 1978.
"Bioelectric Amplifiers", Introduction to Biomedical Equipment Technology by Carr et al., 1981.

*Primary Examiner*—William E. Kamm
*Attorney, Agent, or Firm*—Reed A. Duthler; Harold R. Patton

[57] ABSTRACT

A pacemaker sense amplifier which includes active circuitry which establishes and maintains a constant field density between two electrode poles, effectively clamping them together at a substantially fixed potential difference. The amount of current or power required to maintain this condition in the steady state is monitored and forms the basis of detection of the passing depolarization wavefront.

28 Claims, 8 Drawing Sheets

SENSOR FOR DETECTING CARDIAC DEPOLARIZATIONS PARTICULARLY ADAPTED FOR USE IN A CARDIAC PACEMAKER

This is a continuation of copending application(s) Ser. No. 07/566,636 filed on Aug. 10, 1990 and now abandoned.

BACKGROUND OF THE INVENTION

1. Field of the Invention

This invention relates to implantable pacemakers and more particularly to an improved cardiac interface which includes a new type of sense amplifier.

2. Description of the Prior Art

The cardiovascular system provides oxygenated blood to various structures of the body. The body's demand for oxygenated blood is reflected by the rate at which the sinus node of the heart beats. The electrical signal generated by the sinus node causes the atria or upper chambers of the heart to contract, forcing blood into the lower chambers or ventricles of the heart. After a brief delay, the lower chambers of the heart contract forcing the blood through out the body. The contraction of the ventricles proceeds in an organized fashion which is reflected by the passage of a depolarization wavefront through the syncytium of the heart muscle.

Various disease mechanisms cause conduction disturbances which interfere with the natural conduction system of the heart. A variety of implantable medical devices have been developed to treat these abnormalities. The pacemaker is an example of one such implantable medical device which supplies therapeutic stimulation to the heart to compensate for these conduction defects. Pacemakers as well as other implantable medical devices require interface circuitry which is used to interconnect cardiac sensing circuits and cardiac stimulating circuits to the heart.

The first pacemakers paced the heart at a metronomic rate independent of the hearts underlying rhythm. Such pacemakers are typified by U.S. Pat. No. 3,057,356 to Greatbatch. One problem with such pacemakers is that they may compete with the heart's underlying rhythm and provoke lethal arrhythmias.

The demand pacer was introduced to overcome this defect. This form of pacer contains circuitry to detect the depolarization of the cardiac tissue. The circuitry for performing this function is referred to as a sense amplifier in this art. The function of the sense amplifier is to generate a sense event signal which is used by the escape interval timer of the pacer to resynchronize the pacer to the heart's rhythm. In operation the pacer escape interval timer is set to a nominal stimulation rate which reflects the lowest permissible heart rate. If the underlying heart rate is above this standby rate, the pacer detects the cardiac depolarization and prevents the delivery of pacing stimuli. This form of pacer is now classified as a VVI mode pacer and is taught to the art by U.S. Pat. No. 3,345,990 to B. Berkovitz. The efficacy and safety of this pacing modality requires a reliable sensor of heart activity.

The sense amplifier itself has undergone steady development and refinement as reflected by the teachings of U.S. Pat. No. 4,275,737 to D. Thompson; U.S. Pat. No. 4,379,459 to M. Stein; and U.S. Pat. No. 4,644,931 to R. Beck. However throughout this development, the underlying design philosophy has remained the same.

In the prior art, it has been common to use very high impedance amplifiers which do not substantially load the signal source to amplify the voltage difference which is generated across the electrode pair by the passage of a cardiac depolarization. This prior approach suffers from a variety of problems which relate to the use of high gain factors necessitated by the low level signal generated by the heart. These prior art techniques rely on pass band filters and forms of time domain filtering to achieve acceptable results.

This prior art sense amplifier architecture is easily saturated by the pacing pulse. For this reason, the pacer output stage may be decoupled or isolated from the pacer sense amplifier to help prevent erroneous detection of the pacing artifact. In general, contemporary pacers adopt "blanking", "refractory periods" and "fast recharge" structures to minimize the effects of the interaction between the output stage and the sense amplifier.

It is also possible to minimize interaction between the sensing and pacing functions by dedicating separate electrodes to the pacing and sensing functions. However, lead size and pacer can feedthrough considerations usually dictate lead systems in which electrodes are used for both functions.

SUMMARY OF THE INVENTION

In contrast to this prior art approach, the present invention utilizes active circuitry connected to the lead system to load the two electrode poles to measure the amount of current injected into the lead system by the passing wavefront.

This detection system is especially suited to systems in which pacing and sensing functions share electrode poles since this detection strategy is relatively insensitive to the so called "electrode polarization" effects caused by the delivery of pacing energy to excitable tissue, through a lead system.

In operation, the active circuitry establishes and maintains the electric field density required to maintain an equilibrium condition between the two poles. The field perturbation caused by the passing wavefront is nulled out by the active circuitry which attempts to balance the potentials at the electrodes.

In operation, the amount of current supplied to the electrode surfaces through a virtual load, that is required to maintain this null condition, is monitored and forms the basis for the detection of the passing depolarization wavefront. It is preferred to also monitor the voltage across the virtual load and multiply it with the current measurement to characterize the power delivered to the electrode system by the passing depolarization wavefront.

Thus, in a preferred embodiment, the cardiac depolarization is separated from noise based upon the power level of the depolarization signal. Although this form of detector is disturbed, both by the delivery of pacing energy to the lead system and by the recharge of the output capacitor, the system recovers very quickly.

BRIEF DESCRIPTION OF THE DRAWINGS

In the drawing, like reference numerals indicate corresponding structures throughout the several views in which.

DETAILED DESCRIPTION OF THE PREFERRED EMBODIMENT

In the following description, reference is made to an illustrative embodiment for carrying out the invention. It is understood that other embodiments may be utilized without departing from the scope of the invention.

Figure 1:
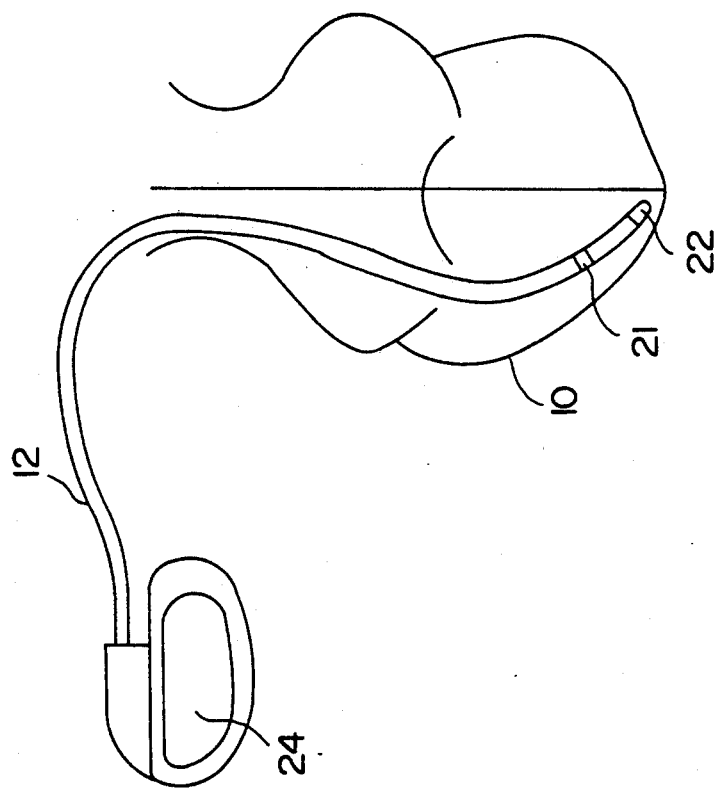
FIG. 1 is a schematic diagram depicting the interconnection between the pacer and the heart.

FIG. 1 is a schematic diagram depicting the interconnection between the pacer and the heart. As shown in the figure, the pacer system comprises a pacing lead or catheter 12 and a pacemaker or pacer 14. The catheter 12 system is passed through a vein into the right ventricle of the heart. The pacemaker 14 is usually implanted subcutaneously outside the rib cage. The catheter is electrically connected to the pacer pulse generator.

There are two basic electrical configurations for pacing leads 12. Unipolar electrode systems include a single tip electrode 22 which is referenced to a can electrode 24. A bipolar lead system adds a ring electrode 21 to the lead 12 as well. This ring electrode may be used as the active sensing electrode or as the reference electrode for either sensing or pacing.

In use, the implanted pacer is typically implanted subcutaneously in the pectoral region. This electrode configuration places at least one electrode 22 within the heart, and another electrode 24 proximate the outside of the heart, with the syncytium of the heart located between the electrode poles. Typically, the distance between the distal tip electrode 22 and the pacer can electrode 24 is between 10 and 30 cm. Conventional tip electrode areas are approximately 8 square mm. While conventional ring electrode areas are approximately 50 square mm. The metallic surface of the pulse generator can serve as the indifferent or reference electrode for either sensing or pacing. The pacer can area is typically on the order of 1000 square mm.

In either the bipolar or unipolar configuration, the distal tip electrode contacts the myocardium. The ring electrode typically is mounted approximately 28 mm proximal to the tip electrode and does not normally contact the myocardium.

Usually, the pacing catheter or lead 12 is used for supplying pacing pulses to the heart and is used for conducting electrical signals resulting from the depolarization of the heart to the pacemaker 14. It is common for the sensing and pacing functions to share at least one electrode pole. Usually both poles are shared.

Figure 2:
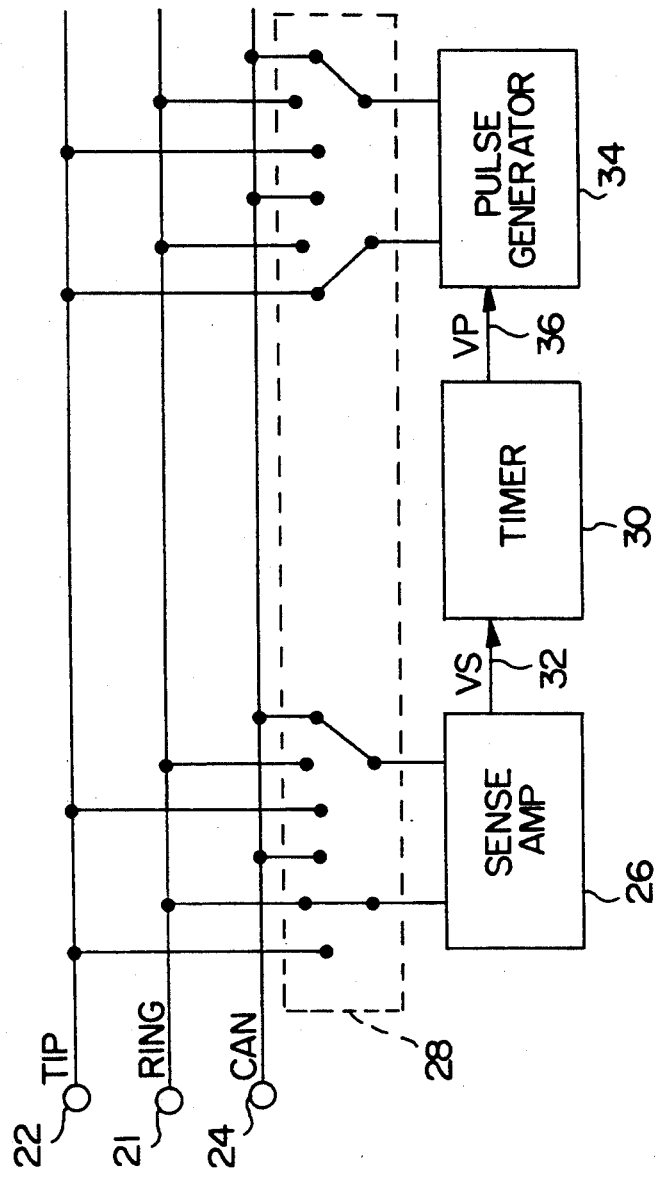
FIG. 2 is a block diagram depicting the relationship between the sense amplifier and the other pacer circuitry.

FIG. 2 depicts the major circuit elements contained within the pacer. In this figure, a hypothetical switch bank or multiplexor 28 is depicted to illustrate the independent selection of the lead configuration for the pacing function and for the sensing function. In the figure, the ring electrode 21 and the can electrode 24 are connected to the sense amplifier 26 for the sensing function, while the tip electrode 22 and the can electrode 24 are coupled to the pulse generator circuit 34.

In operation, the sense amplifier 26 detects the occurrence of the cardiac depolarization and generates a ventricular sense signal (VS) which is coupled to the escape interval timer 30 through an electrical connection 32. Typically, the escape interval timer is remotely programmed to a ventricular escape interval which corresponds to the desired maximum time interval between heartbeats. The occurrence of a ventricular sense events (VS) resets the escape interval timer and thus resynchronizes the pacer to the underlying rhythm of the patient's heart. If no ventricular sense events occurs within the escape interval the escape interval timer times out and generates a ventricular pace signal (VP) which is provided to the pulse generator circuit 34 through a suitable electrical connection 36. The output of the stimulation pulse generator is electrically coupled to the lead system and delivers a suitable stimulation pulse to the myocardium. If the pacer is manufactured to a specific lead configuration, the switch bank will not be required.

Figure 3:
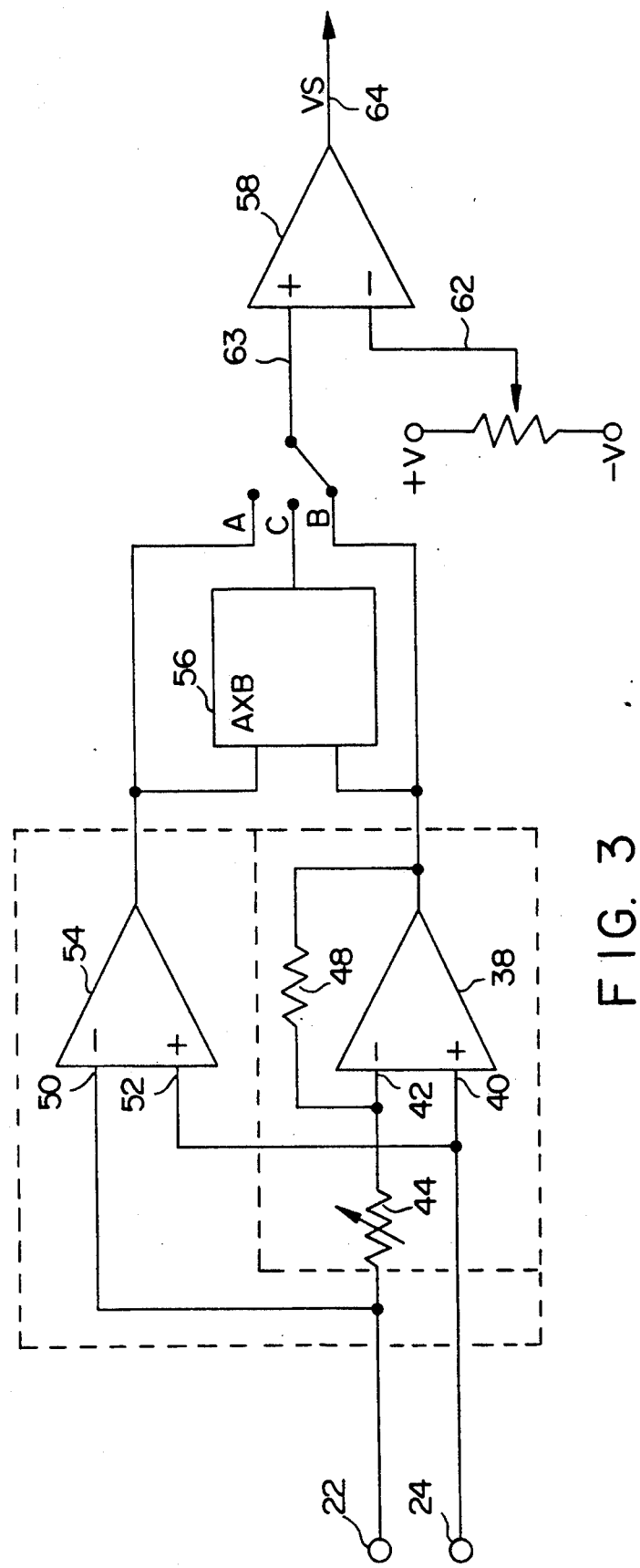
FIG. 3 is a schematic diagram of an illustrative circuit for carrying out the invention.

FIG. 3 is a schematic diagram of an illustrative circuit for carrying out the invention. The circuit may be connected for use as a sense amplifier 26 in the context of a pacer.

The invention may be practiced with a first operational amplifier (op amp) 38 which has a non-inverting input 40 connected to the reference can electrode 24. The inverting input 42 is connected to the tip electrode 22 which operates as a probe electrode through a variable resistor 44 which is used to set a virtual load resistance for the system. A feedback path is provided for the amplifier 38 by a resistance 48 which converts input current to a proportional voltage. In operation the op amp 38 provides a signal at output B which reflects the amount of current required to maintain the electrodes 22 and 24 at the virtual load constrained potential. A second, differential amplifier 54 may be provided to measure the magnitude of the potential difference across the electrode pair. The non-inverting input 50 of this differential amplifier 54 is coupled to one electrode 24, in this case the tip electrode 22 while the can electrode is coupled to inverting input 52. These connections could, of course, be reversed without interfering with the functioning of the device. The output A of this differential amplifier is proportional to the voltage difference between the electrode pair 22 and 24. Preferably the voltage A and current B information may be used to compute the power C through the virtual load resistance required to maintain the constrained equilibrium, as this equilibrium is perturbed by the passage of a cardiac depolarization wavefront. However it is possible to use the current signal B, alone to detect the depolarization.

In the figure, the power computation C is carried out with an analog multiplier 56 which computes the power level, which is compared to a threshold value 62 set by a comparator 58 to generate a ventricular sense signal VS.

Figure 4:
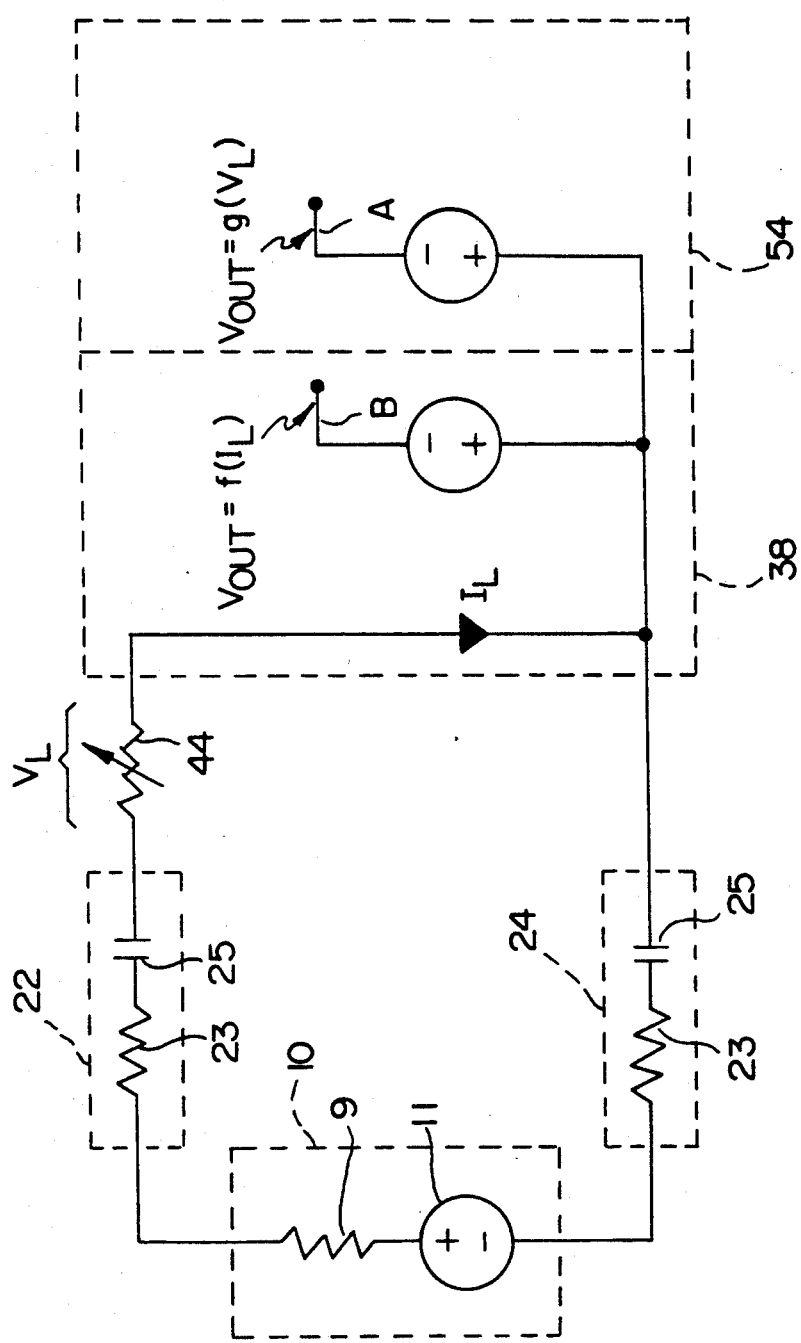
FIG. 4 is a simplified equivalent circuit schematic of the illustrative circuit.

FIG. 4 is a simplified, equivalent circuit schematic of the illustrative circuit shown in FIG. 3. This figure is useful to explain the circuit functions and the circuit interaction with the heart. In this figure the heart 10 has been replaced with its Thevenin equivalent voltage source 11 in series with a source impedance 9. The electrodes have been replaced by their equivalent circuits. In the figure each electrode is modeled as a resistance 23 in series with a capacitance 25. The circuit is closed by the virtual load which is shown as a variable resistor 44. In operation, the operational amplifier 38 measures the amount of current (IL), which is developed through the virtual load 44, during the passage of a depolarization wavefront past the electrode system. The differential amplifier 54 operates to generate a measurement A of the voltage differential generated by the heart as measured across load register 44. This differential measurement portion of the circuit operates in a fashion analogous to traditional prior art sense amplifiers.

To maximize the amount of power through the virtual load it is important to match the value of the virtual load to the lumped value of the access resistances of the electrodes and leads and the source impedance 9 of the Thevinin equivalent of the heart 10. To maximize the current that is supplied to the electrode surface, R44 should be set as close to zero as is practicable. In many instances, setting the virtual load resistance to this optimum value will optimize the signal-to-noise ratio of the system for the detection of the heart signal. However, for other applications it may be desirable to vary the virtual load resistance. In the figure, one can surmise that the lead resistances as well as the source impedance of the heart are parameters that affect the optimal value for the virtual load 44. Experimental evidence indicates that the lumped value of these parameters may vary from a low value of approximately 50 Ohms up to a value of approximately 5000 Ohms, for mammalian hearts and pacing leads of conventional materials and dimensions.

For example, given a conventional pacing lead it is preferred to use a virtual load of less than 100 Ohms. This preferred value and the range of values given reflects the fact that at low values for the virtual load resistance, the electrode and its interface with the tissue becomes a significant circuit parameter. This is in contrast to the prior art where the impedance properties of the electrode are insignificant in comparison to the high input impedance of the amplifier.

Experimental evidence indicates that a field density sensor requires a peak R-wave current of 0.5 microamps flowing to a 1 mm$^2$ polished platinum ring electrode. This data suggests that it is desirable to use electrodes exhibiting surface areas extending from 0.025 to 5 square millimeters. This is in contrast to conventional pacing leads which may exhibit areas which are an order of magnitude larger.

Figure 5:
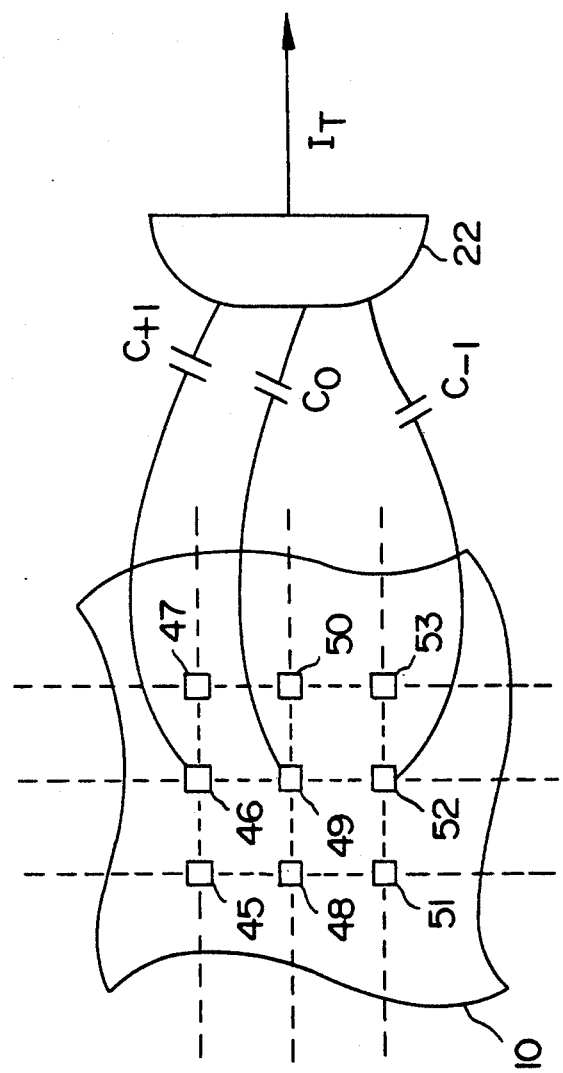
FIG. 5 is a equivalent circuit schematic which models the cardiac tissue and the electrodes.

FIG. 5 is a equivalent circuit schematic which models the cardiac tissue 10 and one of the electrode 22 interfaces. The physiologic basis for the improved sense amplifier performance may be understood in connection with this figure, where the interaction between the depolarizable tissue and the virtual load are modeled.

The excitable tissue of the heart 10 may be broken up into a number of finite elements shown in the figure as 45-53. Each of these elements generates a portion of the total signal It. The depolarization wavefront excites the tissue segments 45-53 and its projected energy disturbs the electrode/electrolyte interface boundary equilibrium. If the electrode 22 were unbound this would cause the electrode potential, with respect to some infinitely distant reference electrode, to change through the mechanism of induced charge. However, through the described electronics the electrode is deliberately connected and current is supplied to the electrode which changes the electrode's surface charge density in such a fashion that the potential between the electrode 22 and the reference electrode 14 is maintained at zero volts, in the case of R1 44 being set to zero. As the myocardial depolarization and the associated disturbance moves away from the local electrode area the need for the excess surface charge is reduced and is then actively recovered from the electrode by the circuit. This charge shuffling is the generated signal of the circuit. With this as a description of the basic mechanism and referring back to FIG. 5 the signal from each segment is coupled through a segment capacitance. The value of this capacitance is a function of the segments distance from the electrode 22. In general the more remote locations are coupled by a smaller capacitance. The exact form of the function is unknown, however it appears to be well modeled as an exponential function. It also appears that electrode material choice may affect the value of this capacitance. As an example of this, the coupling capacitance valve of platinum is higher than for zirconium. In FIG. 3 representative segment capacitances are labeled as C0, C−1, C+1, wherein the number represents the relative distance of the element from the geometric origin of the electrode pole.

Figure 6:
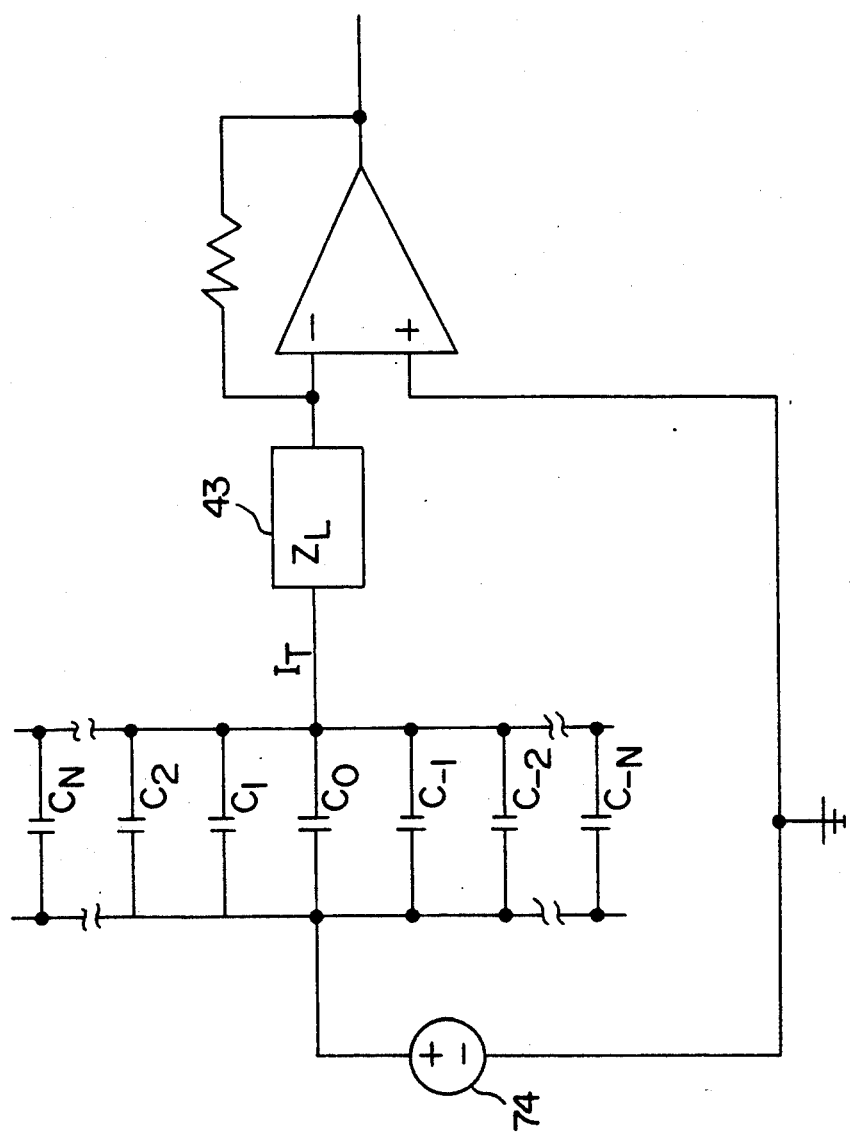
FIG. 6 is a schematic diagram used to model the performance of the circuitry.

FIG. 6 is a schematic diagram used to model the performance of the circuitry. In this figure the tissue directly under the electrode is coupled by capacitance C0, while the more remote segments are coupled by capacitances labeled with positive and negative numbers; for example, the Nth segment is coupled by the Nth capacitance. The access resistances, the electrode resistances, the source impedance 9 and the virtual load value 44 are modeled by element 43 (FIG. 6). This equivalent circuit was modeled to give the signal contribution curves set forth in FIGS. 7-10.

Figure 7:
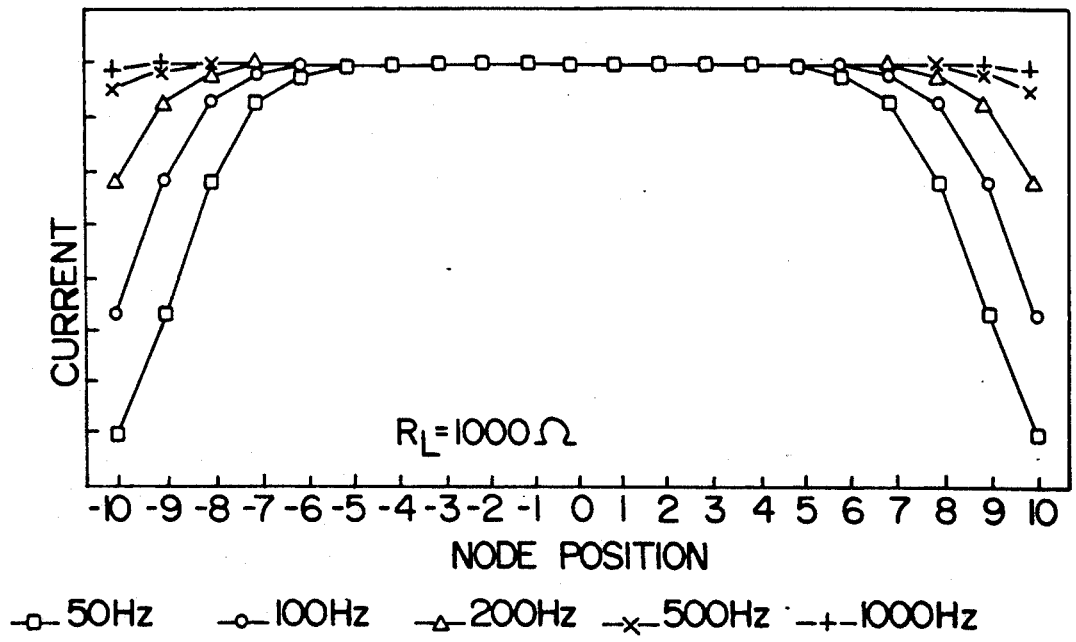
FIG. 7 is a plot of data showing the relationship between design variables and the performance characteristics of the sense amplifier.

FIG. 7 is a plot of data showing the relationship between design variables and the performance characteristics of the sense amplifier. In this figure the abscissa displays the location of the excitable tissue segment of the heart. The origin is taken as the point directly beneath the geometric center of the probe electrode surface. In the figure the virtual load resistance is set equal to 1000 Ohms. This is a relatively large value for the virtual load when the circuit is used as a traditional sense amplifier. The family of curves represent excitable tissue segments operating as sinusoidal oscillators at frequencies from 50 Hz to 1000 Hz. The total signal is proportional to the summed areas under the curves. FIG. 7 shows substantial signal contribution from remote segments (N= ±10), especially at the higher frequencies.

Figure 8:
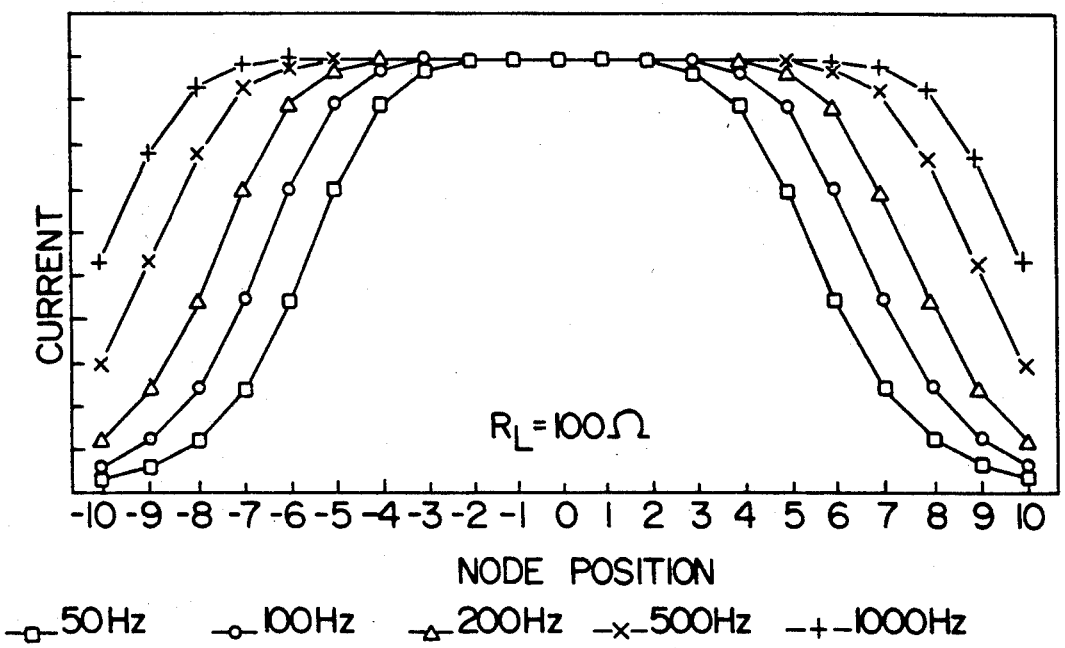
FIG. 8 is a plot of data showing the relationship between design variables and the performance characteristics of the sense amplifier.

FIG. 8 is a plot of data showing the relationship between design variables and the performance characteristics of the sense amplifier. In this example the value of the lumped resistance 43 is 100 Ohms. This family of curves shows that the selection of the value for the virtual load resistance 44 controls the signal contribution volume. In essence, the actual volume of excitable tissue which effectively contributes to the signal can be controlled by the selection of the virtual load value.

Figure 9:
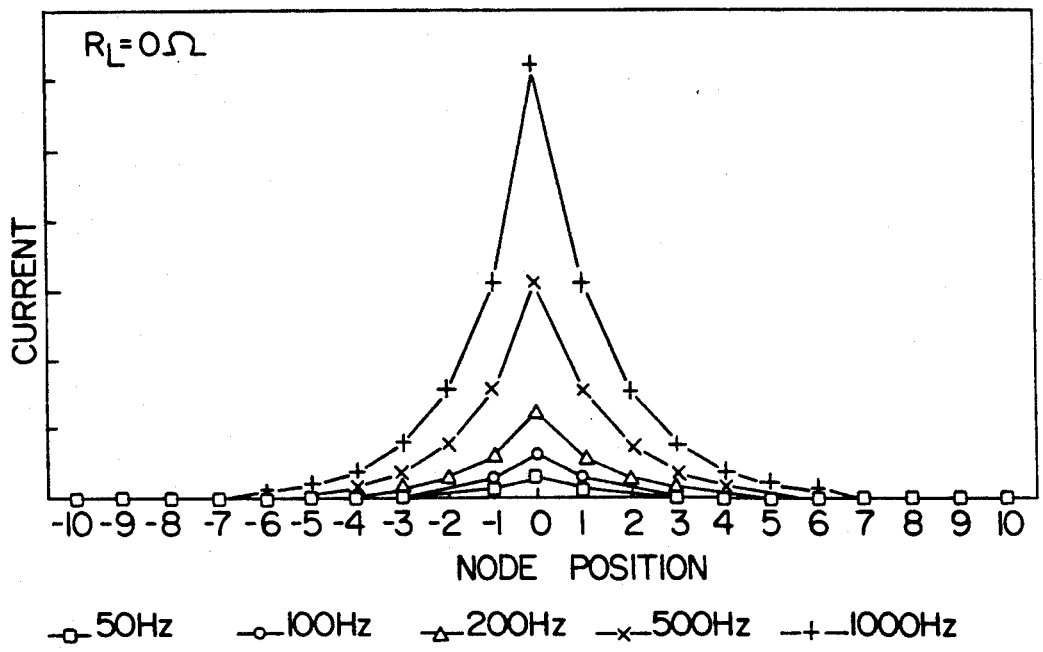
FIG. 9 is a plot of data showing the relationship between design variables and the performance characteristics of the sense amplifier.

FIG. 9 is a plot of data showing the relationship between design variables and the performance characteristics of the sense amplifier. In this instance the virtual load resistance is made as small as possible and is modeled as zero ohms. In this instance the volume of excitable tissue generating the signal is quite small and is centered directly under the electrode. In the case of an extremely low load impedance, modeled here as zero ohms, the signal contribution falls off quite rapidly with increasing distance from the electrode. This characteristic is the basis for some of the performance of the improvements provided by the present invention as compared to prior art high impedance sensing techniques.

Figure 10:
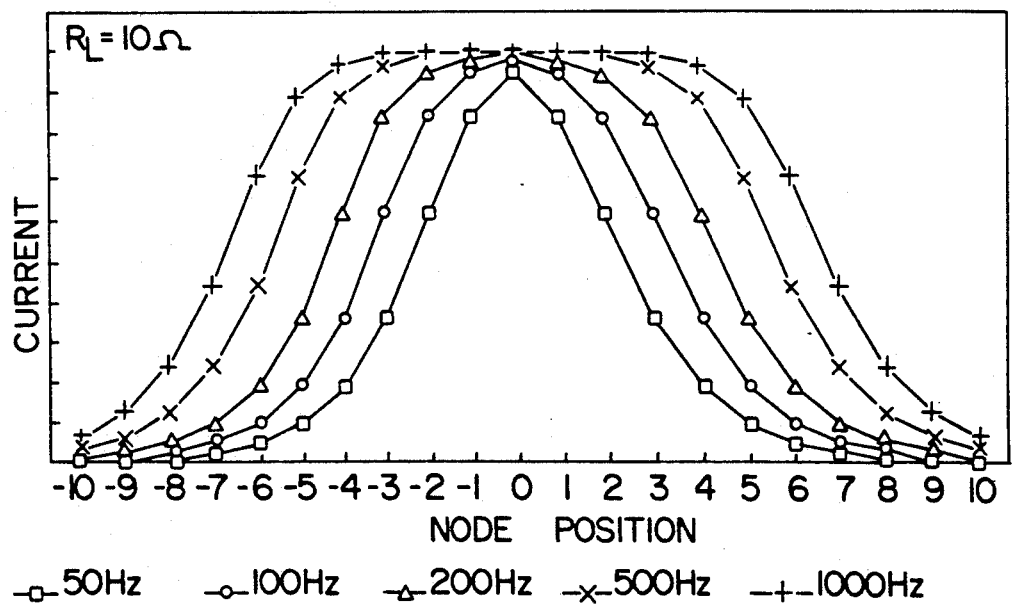
FIG. 10 is a plot of data showing the relationship between design variables and the performance characteristics of the sense amplifier.

FIG. 10 is a plot of data showing the relationship between design variables and the performance characteristics of the sense amplifier. In this example the value of the lumped load is taken as 10 Ohms. In contrast to the representation of FIG. 9 the signal contribution volume is relatively large. This effect suggests that electrode capacitance geometry and resistance can be used as circuit parameters to adapt the lead system to the physiologic system generating the depolarization signals.

What is claimed is:

1. Cardiac interface apparatus, for detecting the passage of a cardiac depolarization wavefront in the myocardium, and generating a sense event signal; and for providing stimulating energy in response to a pace event signal, to the myocardium to provoke a contraction of the myocardium, comprising:
    a first, probe electrode for location proximate said myocardium;
    a second, reference electrode;
    a virtual load connected to said first electrode;
    charge supplying means coupled to said virutal load and to said second electrode for maintaining said first electrode at a steady state of electrical potential relative to said second electrode;
    monitoring means for monitoring the current through said virtual load means required to maintain said steady state during the occurrence of a cardiac depolarization
    and for generating a sense detect signal when said current exceeds a threshold; and
    pulse generator means coupled to at least one of first and second electrodes for delivering pacing energy in response to said pace event signal.

2. The apparatus of claim 1 wherein said virtual load comprises:
    a resistor in series with said probe and said charge supplying means.

3. The apparatus of claim 1 or claim 2 wherein the value of said virtual load is greater than zero Ohms and less than five thousand Ohms.

4. The apparatus of claim 1 or claim 2 wherein said first electrode has an exposed area of greater than 0.025 square millimeters and less than 5.0 square millimeters.

5. The apparatus of claim 1 or claim 2 wherein said first electrode has an exposed area of less than 5.0 square millimeters.

6. Cardiac interface apparatus, for detecting the passage of a cardiac depolarization wavefront in the myocardium, and generating a sense event signal; and for providing stimulating energy in response to a pace event signal, to the myocardium to provoke a contraction of the myocardium, comprising:
    a first, probe electrode for location proximate said myocardium;
    a second, reference electrode for location proximate said myocardium;
    a virtual load connected to said first electrode;
    charge supplying means coupled to said virtual load and said second electrode for maintaining said first electrode at a steady state potential with respect to said second electrode;
    monitoring means for monitoring the current through said virtual load required to maintain said steady state potential during the occurrence of a cardiac depolarization
    and for generating a sense detect signal when the transduced value of said current exceeds a threshold;
    third, stimulating electrode for location proximate said myocardium;
    forth, stimulating electrode for location proximate said myocardium;
    pulse generator means coupled to third and fourth electrodes for delivering pacing energy to said myocardium in response to said pace event signal.

7. Apparatus for detecting the passage of a cardiac depolarization wavefront in the myocardium comprising:
    a first electrode for location inside the heart;
    a second electrode for location outside the heart;
    a virtual load connected to said first electrode;
    charge supplying means coupled to said virtual load and said second electrode for maintaining said first electrode at a steady state potential relative to said second electrode;
    monitoring means for monitoring the current through said virtual load means
    and for generating a sense detect signal for indicating the occurrence of said cardiac depolarization.

8. The apparatus of claim 7 wherein said charge supplying means comprises:
    an operational amplifier having inverting and non-inverting inputs, and having an output, said charge supplying means further comprising a feedback impedance connected between said inverting input and said output;
    said non-inverting input being connected to said reference electrode means; and
    said inverting input being connected to said virtual load means.

9. In a cardiac stimulation apparatus comprising means for generating cardiac stimulating pulses for application to a patient's heart and means detecting depolarizations of said patient's heart, the improvement wherein said detector means comprises:
    first and second electrodes for sensing cardiac signals;
    a virtual load connected to said first electrode;
    an active circuit, coupled to said second electrode and said virtual load, for providing electrical energy to said first electrode through said virtual load in response to the occurrence of a cardiac depolarization to counteract depolarization induced variation in the relative electrical potentials of said first and second electrodes;
    a monitoring circuit, coupled to said active circuit, for monitoring electrical current provided through said virtual load, for detecting the occurrence of a cardiac depolarization.

10. The apparatus of claim 9 wherein said virtual load provides a resistance between 0 and 5000 ohms.

11. The apparatus of claim 9 wherein said virtual load provides a resistance between 0 and 1000 ohms.

12. The apparatus of claim 9 wherein said virtual load provides a resistance between 0 and 100 ohms.

13. The apparatus of claim 9 wherein said monitoring circuit comprises current monitoring circuitry responsive to the current through said virtual load.

14. The apparatus of claim 9 wherein said monitoring circuit comprises circuitry responsive to the power through said virtual load.

15. The apparatus of claim 9 wherein said apparatus further comprises means for adjusting the relative effect of the depolarization of cardiac tissue on the amount of electrical energy applied through said virtual load by said active circuitry as a function of the distance of said cardiac tissue from said first electrode.

16. The apparatus of claim 15 wherein said adjusting means comprises means for adjusting the impedance of said virtual load.

17. The apparatus of claim 9 wherein said first electrode has a surface area of up to 5 square millimeters 18. The apparatus of claim 9 wherein said first electrode has a surface area of between 0.25 and 5 square millimeters.

19. The apparatus of claim 9 wherein said pulse generating means is coupled to said first electrode.

20. Apparatus for detecting depolarization of cardiac tissue, comprising:
   first and second electrodes, said first electrode for location adjacent cardiac tissue;
   first and second electrodes, said first electrode for location adjacent cardiac tissue;
   an active circuit means coupled to said first and second electrodes for providing electrical energy to said first electrode in response to the occurrence of a cardiac depolarization to counteract depolarization induced variation in the relative electrical potentials of said first and second electrodes;
   wherein said active circuit means comprises an operational amplifier having first and second inputs, an output and means for providing an electrical output signal, said active circuit means further comprising a feedback impedance connected between said second input to said operational amplifier and said output, said apparatus further comprising a virtual load impedance connected between said first electrode and said first input and means for connecting said second electrode to said second input; and
   a monitoring circuit coupled to said output of said operational amplifier for detecting the occurrence of cardiac depolarizations.

21. The apparatus of claim 20 wherein said virtual load provides an impedance of between 0 to 1000 ohms.

22. The apparatus of claim 20 wherein said virtual load provides an impedance between 0 and 100 ohms.

23. The apparatus of claim 20 or 21 or 22 wherein said monitoring circuit comprises means for comparing said electrical signal at the output of said operational amplifier to a predetermined criterion to detect the occurrence of said depolarization.

24. The apparatus of claim 23 wherein said monitoring circuit comprises means for comparing the voltage of said electrical signal at the output of said operational amplifier to a predetermined voltage threshold to detect the occurrence of said depolarization.

25. The apparatus of claim 23 wherein said monitoring circuit comprises power measuring circuitry measuring the power through said virtual load to detect the occurrence of said depolarization.

26. The apparatus of claim 20 further comprising adjusting means for adjusting the impedance of said virtual load.

27. The apparatus of claim 20 wherein said first electrode has a surface area of up to 5 square millimeters.

28. The apparatus of claim 20 wherein said first electrode has a surface area of 0.25 to 5 square millimeters.

* * * * *